(12) United States Patent
Miksza et al.

(10) Patent No.: US 9,662,100 B2
(45) Date of Patent: May 30, 2017

(54) TISSUE WOUND CLOSURE DEVICE AND APPLICATOR INSTRUMENT

(71) Applicant: Ethicon, Inc., Somerville, NJ (US)

(72) Inventors: Anthony Miksza, Nazareth, PA (US); Jianxin Guo, Livingston, NJ (US); Jonathan Bennett Gabel, Randolph, NJ (US)

(73) Assignee: Ethicon, Inc., Somerville, NJ (US)

( * ) Notice: Subject to any disclaimer, the term of this patent is extended or adjusted under 35 U.S.C. 154(b) by 129 days.

(21) Appl. No.: 14/722,729

(22) Filed: May 27, 2015

(65) Prior Publication Data

US 2016/0345942 A1    Dec. 1, 2016

(51) Int. Cl.
| | |
|---|---|
| *A61B 17/08* | (2006.01) |
| *A61D 1/00* | (2006.01) |
| *A61B 17/00* | (2006.01) |
| *A61B 17/06* | (2006.01) |
| *A61B 17/04* | (2006.01) |
| *A61B 17/062* | (2006.01) |

(52) U.S. Cl.
CPC ...... *A61B 17/0057* (2013.01); *A61B 17/0469* (2013.01); *A61B 17/0483* (2013.01); *A61B 17/062* (2013.01); *A61B 17/06166* (2013.01); *A61B 2017/00663* (2013.01); *A61B 2017/0472* (2013.01); *A61B 2017/06042* (2013.01); *A61B 2017/06176* (2013.01)

(58) Field of Classification Search
CPC ...... A61B 2017/06176; A61B 17/0469; A61B 17/06166; A61B 2017/00004; A61B 2017/0461; A61B 17/04; A61B 17/0482; A61B 17/0485; A61B 17/0057; A61B 17/06004; A61B 2017/00623
USPC ....... 606/144, 145, 148, 215, 220, 223, 224, 606/228, 230
See application file for complete search history.

(56) References Cited

U.S. PATENT DOCUMENTS

| | | |
|---|---|---|
| 3,825,010 A | 7/1974 | McDonald |
| 4,430,998 A | 2/1984 | Harvey et al. |
| 4,637,380 A | 1/1987 | Orejola |
| 5,047,047 A | 9/1991 | Yoon |
| 5,234,462 A | 8/1993 | Pavletic |
| 5,342,376 A | 8/1994 | Ruff |
| 5,403,346 A | 4/1995 | Loeser |
| 5,500,000 A | 3/1996 | Feagin et al. |
| 5,683,417 A | 11/1997 | Cooper |
| 5,984,949 A | 11/1999 | Levin |
| 6,176,868 B1 | 1/2001 | Detour |
| 7,021,316 B2 | 4/2006 | Leiboff |
| 7,686,829 B2 | 3/2010 | Elliott et al. |
| 8,066,737 B2 | 11/2011 | Meade et al. |
| 8,100,939 B2 | 1/2012 | Peterson |
| 2003/0149447 A1 | 8/2003 | Morency et al. |
| 2005/0240189 A1 | 10/2005 | Rousseau et al. |
| 2009/0093824 A1 | 4/2009 | Hasan et al. |
| 2010/0274283 A1 | 10/2010 | Kirsch et al. |
| 2010/0298871 A1 | 11/2010 | Ruff et al. |
| 2011/0054522 A1 | 3/2011 | Lindh et al. |

(Continued)

*Primary Examiner* — Katherine M Shi

(74) *Attorney, Agent, or Firm* — E. Richard Skula

(57) ABSTRACT

Novel tissue wound closure devices and applicator instruments are disclosed. The tissue wound closure devices have a filament or strap and a capture device that locks the filament or strap in place after application to approximate a wound in tissue. The applicator instruments have a curved insertion needle.

18 Claims, 18 Drawing Sheets

(56) References Cited

U.S. PATENT DOCUMENTS

| | | |
|---|---|---|
| 2012/0053603 A1 | 3/2012 | Williamson, IV |
| 2012/0165838 A1 | 6/2012 | Kobylewski et al. |
| 2013/0267997 A1 | 10/2013 | Peterson et al. |
| 2015/0119907 A1* | 4/2015 | Fenton ............... A61B 17/0469 606/145 |
| 2016/0106421 A1* | 4/2016 | Eliachar ............. A61B 17/0401 606/228 |

* cited by examiner

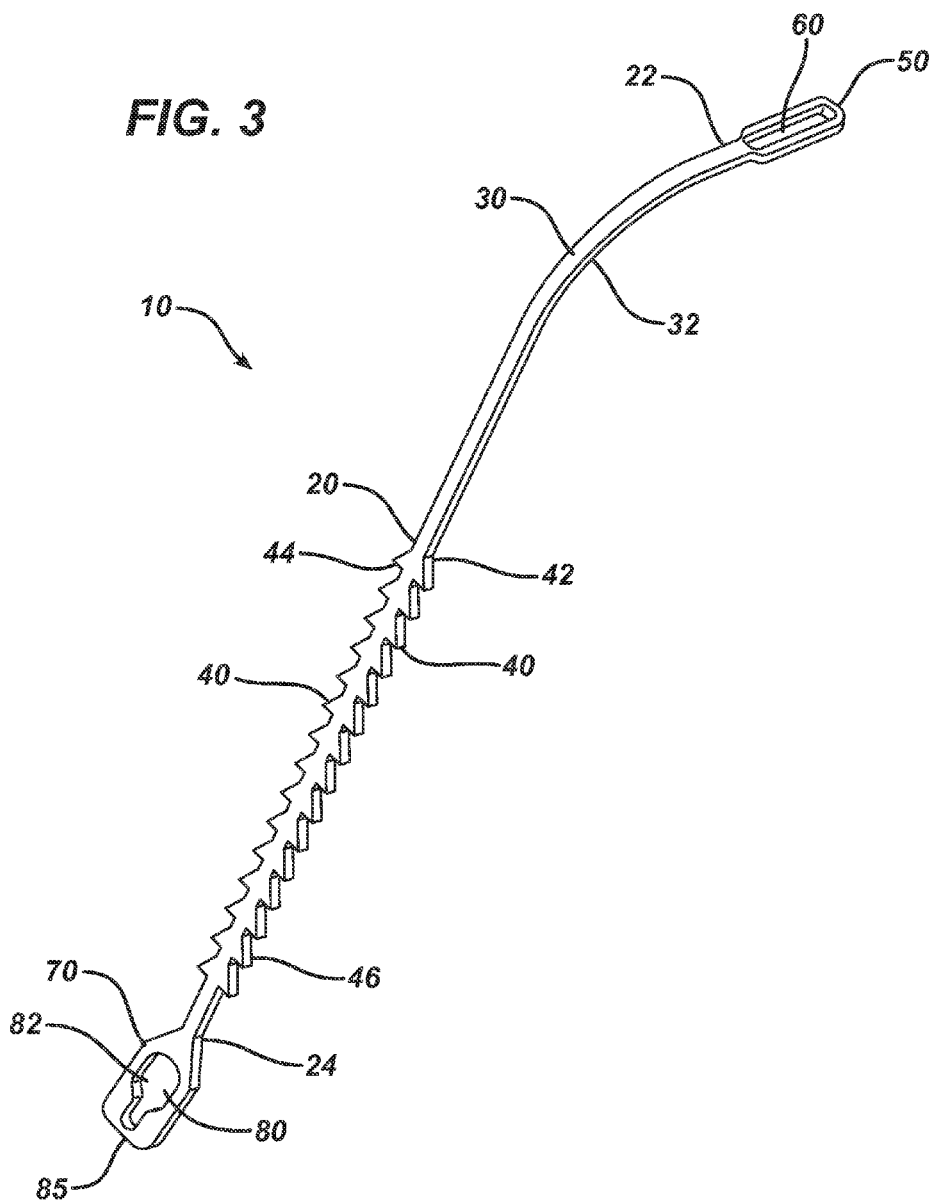

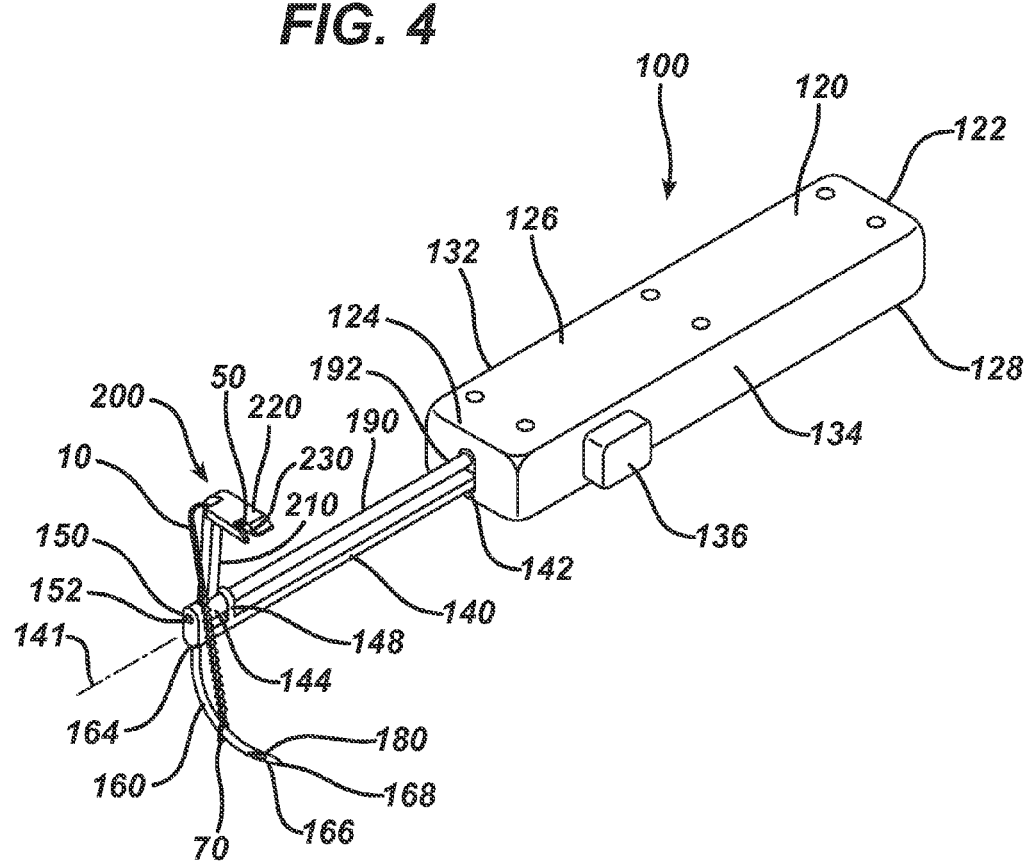

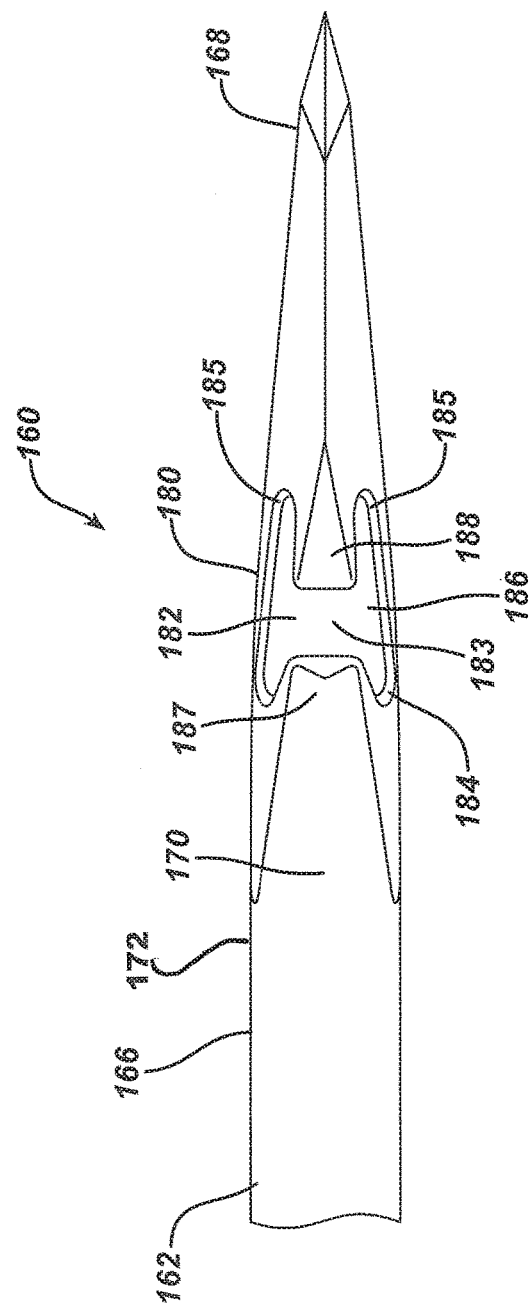

TISSUE WOUND CLOSURE DEVICE AND APPLICATOR INSTRUMENT

FIELD OF THE INVENTION

The field of art to which this invention pertains is tissue repair, more particularly devices and applicator instruments for repairing wounds in tissue.

BACKGROUND OF THE INVENTION

Wounds in tissue are typically repaired using conventional wound closure devices such as surgical sutures and surgical staples. In addition, surgical glues and adhesives have been used to repair certain types of tissue, primarily exterior dermal wounds. In a typical wound caused by trauma or in an incision, the standard of care to repair the wound provides for approximating the opposed sides of the wound using some sort of mechanical device to securely maintain the sides of the closed wound in contact with each other until natural healing occurs. When using surgical sutures to approximate tissue, the suture is often knotted to form stitches in an interrupted suture repair. This knotting process is often difficult and is typically time consuming; additionally, the suturing and knotting process requires that the surgeon use both hands. Time is often of the essence when treating wounds and effecting a wound repair for several reasons, including stopping blood flow and protecting the underlying tissue from infection by pathogens in the environment.

There is a need in this art for novel tissue wound repair devices that are self-locking without the need to tie knots, and associated applicator instruments, for facilitating the repair of wounds in tissue. There is also a need for novel wound closure devices that can be applied and secured by the surgeon with the use of a single hand.

SUMMARY OF THE INVENTION

Accordingly, a novel tissue wound closure device is disclosed. The wound closure device has an elongated member having a proximal end, a distal end, opposed lateral side surfaces, a top surface and a bottom surface. A first tab member extends from the proximal end; the first tab member having a keyhole opening. A second tab member extends from the distal end; the second tab member has an opening. A plurality of barb members extends from at least one surface of the elongated member. The keyhole opening in the first tab member is configured to pass the first tab member through and receive a section of the elongated member, and, to lock a section of the elongated member in a fixed position within the first tab member.

Another aspect of the present invention is a novel apparatus for applying an elongated tissue wound closure device. The apparatus has an elongated handle member having a proximal end and a distal end. A shaft member is rotatably mounted to the handle member and extends from the distal end of the handle member; the shaft member has a longitudinal axis. An actuation member is moveably mounted to the handle member for engaging a linear to rotary motion mechanism in the handle member to cause the shaft member to rotate. A beam member extends from the distal end of the handle member, the beam member has a proximal end and a distal end and a longitudinal axis. A first curved needle member is mounted to the distal end of the beam member. The first curved needle member defines a plane and has a proximal end, a distal end, an inner surface, an outer surface, a capture notch, and a piercing point extending from the distal end. The proximal end of the curved needle member is mounted to the distal end of the beam member such that the plane of the needle member is substantially transverse to the longitudinal axis of the beam member. A first placement member is mounted to the distal end of the shaft member in a manner substantially transverse to the longitudinal axis of the shaft member; the placement member has a post member. The post member has a distal end, and a tab engagement member extending from the distal end and having an engagement notch for receiving a tab member.

Yet another aspect of the present invention is system formed from the combination of a novel tissue wound closure device of the present invention and a novel applicator instrument. The wound closure system has an apparatus for applying a tissue wound closure device. The apparatus has an elongated handle member having a proximal end and a distal end. A shaft member is rotatably mounted to the handle member and extends from the distal end of the handle member; the shaft member has a longitudinal axis. An actuation member is mounted to the handle member for engaging a linear to rotary motion mechanism in the handle member to cause the shaft member to rotate. A beam member extends from the distal end of the handle member; the beam member has a proximal end, a distal end, and a longitudinal axis. A curved needle member is mounted to the distal end of the beam member. The curved needle member has a proximal end, a distal end, an inner surface, an outer surface, a capture notch, and a piercing point extending from the distal end; the curved needle defines a plane. The proximal end of the curved needle member is mounted to the distal end of the beam member such that the plane of needle member is substantially transverse to the longitudinal axis of the beam member. A placement member is mounted to the distal end of the shaft member in a manner substantially transverse to the longitudinal axis of the shaft member; the placement member has a post member. The post member has a distal end and a tab engagement member extending from the distal end and having an engagement notch for receiving a tab member. The tissue wound closure device of the system an elongated member having a proximal end, a distal end, opposed lateral side surfaces, a top surface, and a bottom surface. A first tab member extends from the proximal end, the first tab member has a keyhole opening. A second tab member extends from the distal end, the second tab member has an opening. A plurality of barb members extend from at least one surface of the elongated member. Then the keyhole opening in the first tab member is configured to pass the second tab member through and receive a section of the elongated member, and to lock a section of the elongated member in a fixed position within the first tab member.

Still yet another aspect of the present invention is a method of using the above-described wound closure device and applicator to approximate a wound tissue.

These and other aspects and advantages of the present invention will become more apparent from the following description and accompanying drawings.

BRIEF DESCRIPTION OF THE DRAWINGS

FIG. 3 is a perspective view of the tissue wound closure device of FIG. 2.

FIG. 4 is a perspective view of an applicator device useful to insert the wound closure devices of the present invention; the tissue wound closure device of FIGS. 1-3 is seen to be mounted to the distal end of the applicator device.

FIG. 5B is a magnified top view of the distal end of the needle member of FIG. 5A showing the capture notch.

DETAILED DESCRIPTION OF THE INVENTION

The tissue wound closure devices of the present invention may be made from suitable, conventional biocompatible materials and equivalents thereof. The materials may be absorbable, non-absorbable or combinations of absorbable and non-absorbable materials. Examples of absorbable materials include, but are not limited to, polymers and copolymers such as polydioxanone, polylactide, polylactic acid, ε-caprolactone, polyglycolide, polycaprolactone, trimethylene carbonate, lactide-co-glycolide, glycolide-co-caprolactone, combinations thereof copolymers thereof, and the like. Examples of non-absorbable materials include, but are not limited to, polymers and copolymers such as polyethylene, polypropylene, nylon, polyester and the like. The fastener devices may be manufactured in conventional manners including injection molding, extrusion, stampings, roll forming, die cutting, and the like. The applicator instruments of the present invention may be made from conventional, biocompatible materials, including but not limited to surgical stainless steel, polycarbonate, plastic resins, metals, alloys, combinations thereof and the like. The instruments may be made using conventional manufacturing techniques and processes including injection molding, stamping, machining, forming and the like, and assembled using conventional assembly techniques and processes.

Figure 1:
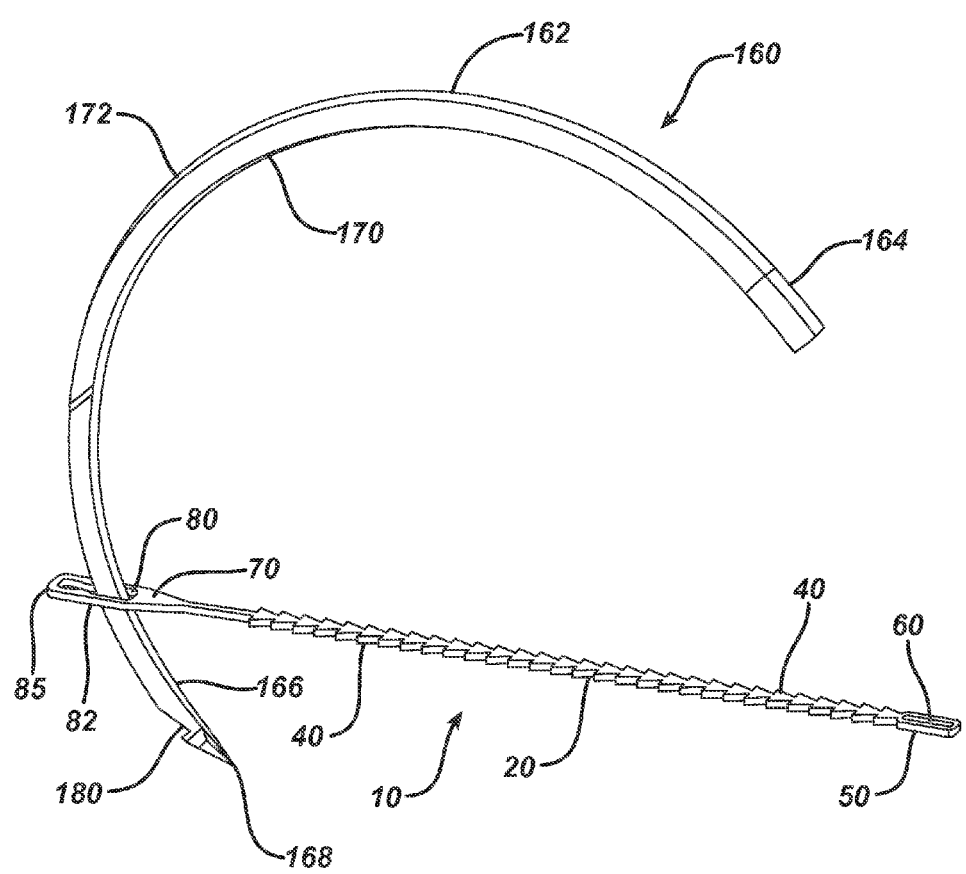
FIG. 1 is a perspective view of a novel tissue wound closure device of the present invention and a tissue piercing needle of an applicator instrument.
Figure 2:
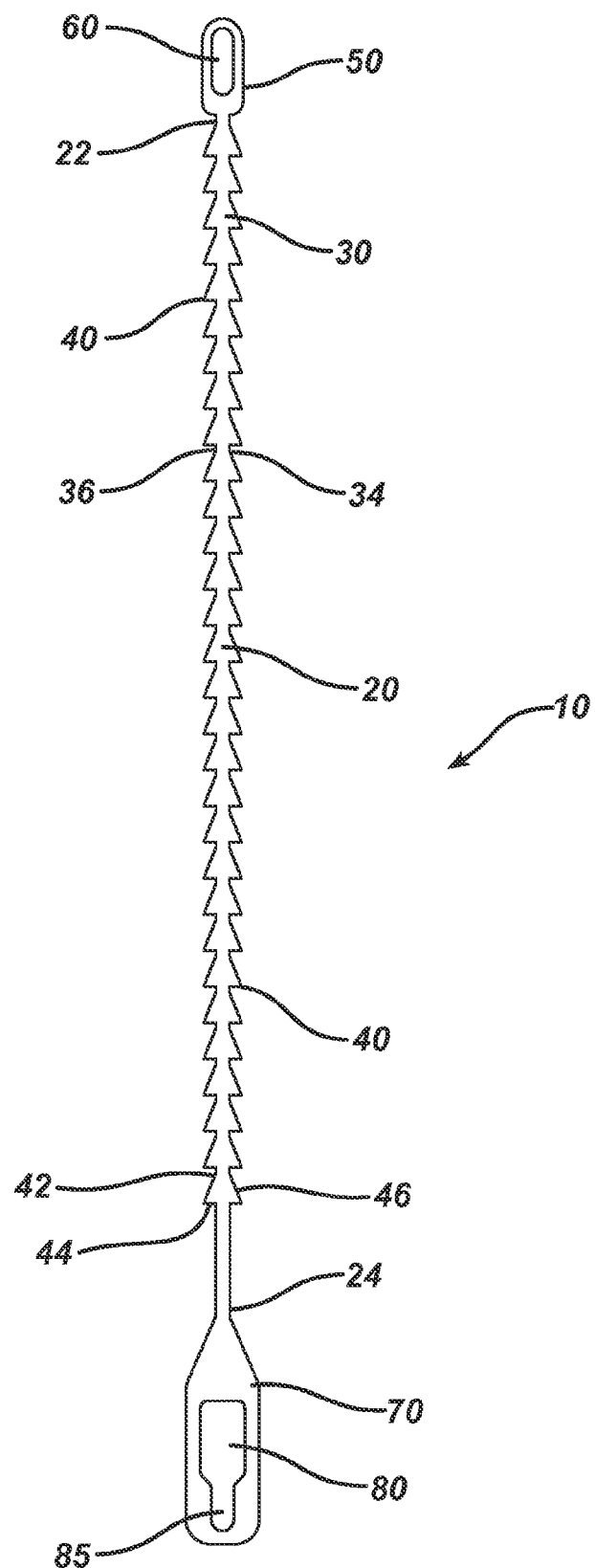
FIG. 2 is a top, plan view of a tissue wound closure device of the present invention.

A tissue wound closure device 10 of the present invention is seen in FIGS. 1-3. Also seen in FIG. 1 is a curved needle member 160 used to apply the tissue wound closure device 10. The closure device 10 is seen to have elongated body member 20. Body member 20 is seen to have distal end 22 and proximal end 24. The body member has top surface 30, bottom surface 32 and opposed lateral sides 34 and 36. Extending outwardly from the lateral sides 34 and 36 are a plurality of barb members 40. The barb members 40 have distal ends 42, proximal ends 44 and sloping surfaces 46 connecting the distal ends 42 and proximal ends 44. As shown, the body member 20 is flat as are the barb members 40. If desired, body member 20 may have a round, curved, or polygonal cross-section, and the barb members may have a truncated conical shape, or other equivalent geometric shapes. Extending from the distal end of 22 of the body member 20 is the distal or second tab member 50. Tab member 50 is seen to have a slot or opening 60 for receiving a section of the body member 20 including barb members 40. Opening 60 is sufficiently sized to effectively allow movement of the body member 20 and barbs 40 through the tab member 50. Proximal or first tab member 70 is seen to extend from the proximal end 24 of the body member 20. Tab member 70 is seen to have keyhole opening 80 for receiving and locking a section of body member 20. The opening 80 has enlarged opening section 82 for receiving and passing through a section of body member 20 and smaller locking opening 85 in communication with section 82 for receiving and locking a section of body member 20. Opening 82 is sufficiently sized to effectively allow movement of the body member 20 and barbs 40 through the tab member 70. The locking function of locking opening 85 is performed by a friction fit plus instantaneous compression and relaxation of the barb members 40 through the openings 82 and 85, and locking can also be achieved by torquing/twisting of the barb member 40 through holes 82 and 85 in one direction so that they cannot come back out after they pass through.

Referring to FIGS. 1, 4 and 5A-C, an applicator instrument 100 and needle member 160 of the present invention used to insert the tissue wound closure devices of the present invention is seen. The instrument 100 is seen to have elongated handle member 120. Handle member 120 is seen to have proximal end 122, distal end 124, top 126, and bottom 128. The handle member 120 is also seen to have opposed lateral sides 132 and 134. Handle member 120 is seen to have a generally flat configuration, but may have other geometric configurations including cylindrical, etc. The push button actuation member 136 is seen to extend outwardly from side 134. The push button actuation member is seen to have a generally cuboid or rectangular cuboid configuration but may have other geometric configurations including cylindrical, semispherical, etc. The push button member 136 as shown is moveably mounted in handle member 120 such that it is moveable by finger actuation toward the side 134, and similarly moveable away from side 134 by a biasing member such as a spring (not shown). If desired, other actuation members and movements may be utilized such as a trigger, a rod, etc. Extending distally from the distal end 124 of handle member 120 in a longitudinal manner is the support beam member 140. Beam member 140 is seen to have longitudinal axis 141. Beam member 140 is also seen to have proximal end 142 and distal end 144. Adjacent to distal end 144 are the shaft bearing support members 148. The distal cap member 150 is seen to be associated with distal end 144. Distal cap member 150 may be a separate piece mounted to the distal end 144, or may be machined or molded as a unitary part of the support beam member 140. Cap member 150 is seen to have optional opening 152 for optionally receiving a section of the distal end 194 of shaft member 190.

The needle member 160 is fixedly mounted to the cap member 150 in a manner substantially transverse to the longitudinal axis 141 of beam member 140, for example perpendicular or angulated. The needle member 160 is seen to have elongated, curved needle body 162 defining a plane. Needle body 162 has proximal end 164 and distal end 166. Tissue piercing point 168 is seen to extend out from distal end 166. The needle body 162 has inner surface 1170 and outer surface 172. Extending into the inner surface 170 adjacent to tissue piercing point 168 is the tab capture notch 180. Alternatively, the capture notch 180 may extend into the outer surface 172 as seen in FIG. 1. As seen in FIG. 5B, the tab capture notch 180 is seen to have groove 182, opening 183 in communication with groove 182, proximal wall 184, distal wall 185, bottom 186, and proximally extending capture member 188 and opposed distally extending capture member 187. Proximally extending and distally extending capture members 188 and 187 are separated by opening 183. The proximal end 164 of the needle body 162 is seen to be mounted to the cap member 1150 such that the plane of the needle 160 is substantially transverse, e.g., perpendicular, to the longitudinal axis 141 of beam member 140, and can rotated with beam member 140 about the axis 141. The shaft 190 is seen to have proximal end 192 and distal end 194. The shaft 190 has a longitudinal axis. The proximal end 192 of shaft 190 is rotatably mounted in the handle member 120. The distal end 194 of shaft 190 is contained in the bearing support members 148. Actuation of the push button actuation member 130 causes the shaft 190 to rotate with respect to handle member 120 and beam member 140 through a conventional mechanism for converting linear motion (either perpendicular or inline) to rotary motion such as a cam, screw thread, rack and pinion, worm gear, and the like. Mounted to the distal end 194 of shaft 190 is the needle tip placement member 200. Placement member 200 is seen to have radially extending post member 210 having proximal end 212 and distal end 214. Placement member 200 is mounted substantially transverse to the longitudinal axis of shaft member 190, e.g., perpendicular or angulated. Rotation of shaft 190 causes the member 200 to rotate. The tab engagement member 220 is seen to extend perpendicularly out from the distal end 214 of post member 210, but may be optionally angulated otherwise if desired. Engagement member 220 is seen to have top side 222, bottom side 224, proximal end 226 and distal end 228 having ramp section 229. Extending through the distal end 228 of engagement member 220 is the tab holding notch 230. The notch 230 is seen to have back wall 232, opposed side walls 234, opening 236 and open side 238 in communication with opening 236.

Figure 5A:
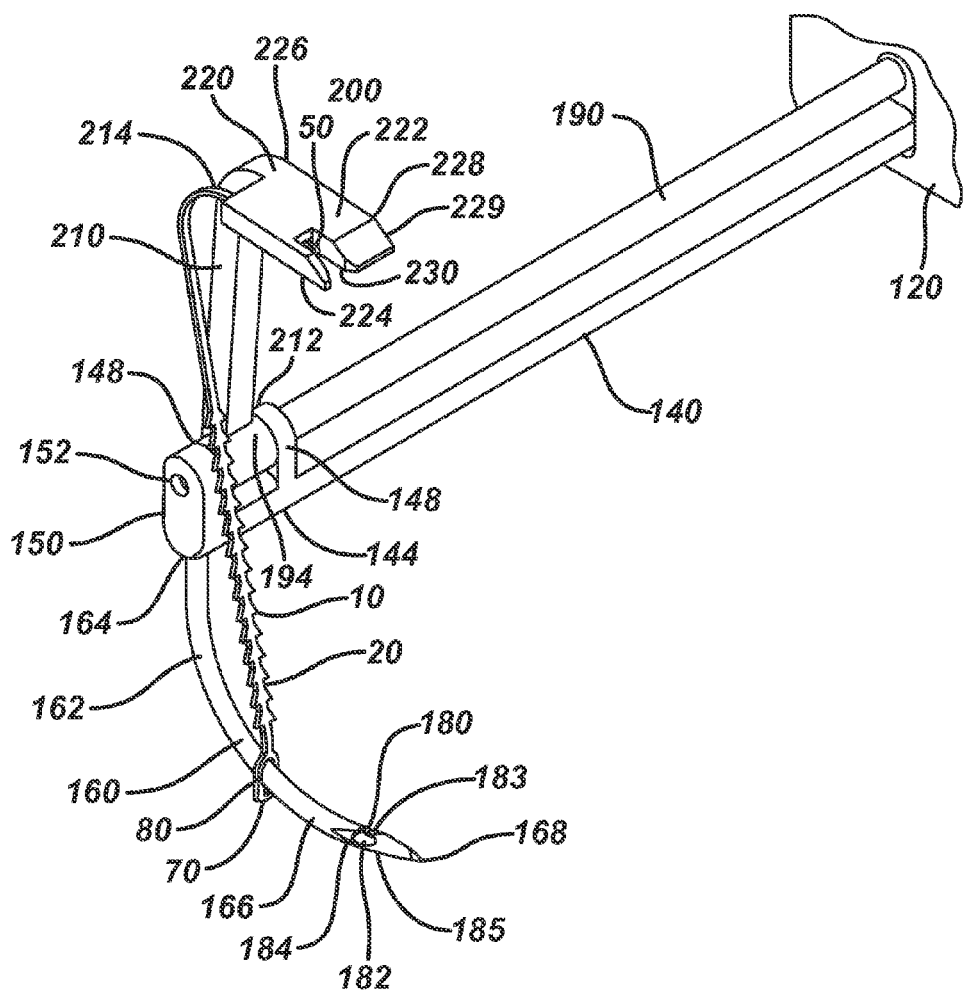
FIG. 5A is a magnified, partial perspective view of the distal end of the applicator of FIG. 4 showing the needle member and the needle tip placement member; a tissue closure device of the present invention is seen to have the distal tab member mounted to the placement member and the proximal tab member mounted on the body of the needle member.
Figure 5C:
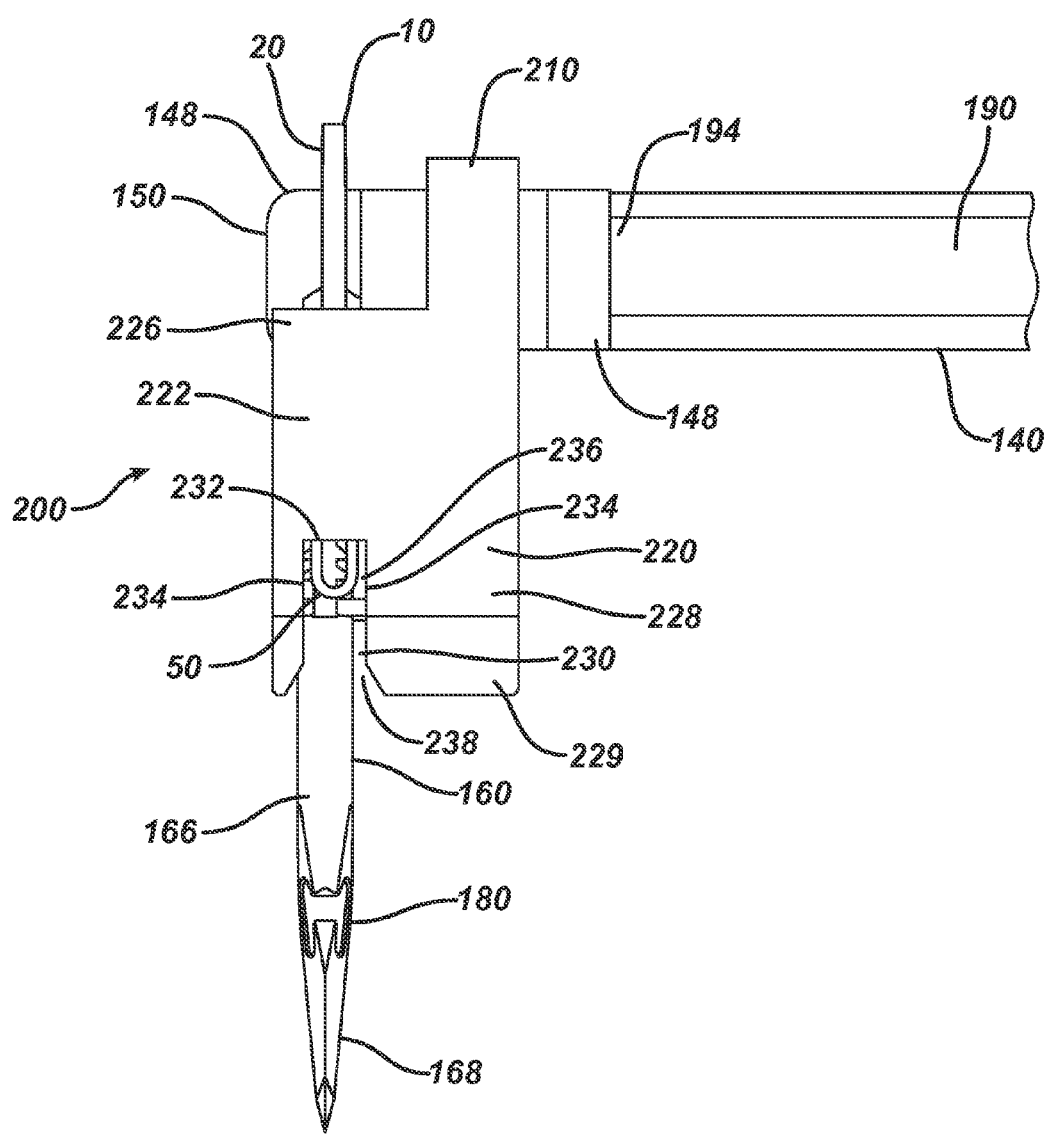
FIG. 5C is a top view of the needle tip placement member of FIG. 5A also showing the distal end of the applicator along with the needle member.

As seen in FIGS. 4, 5A, and 5C, a tissue wound closure device 10 is mounted to the applicator instrument 100 by sliding the proximal tab member 70 over the distal end 166 of the needle 160 such that the tab member 70 is positioned toward the middle of the needle body 162 with a section the needle body 162 contained in the opening section 82 of the keyhole opening 80. The distal tab member 50 is seen to be mounted in the opening 236 of the notch 230 of engagement member 220. A section of the distal end 22 of body member 20 is located beneath bottom side 224 of engagement member 220. Actuation of the actuation button member 136 causes shaft 190 to rotate resulting in the rotation of placement member 200 toward the distal needle tip end 166 and piercing point 168 such that the piercing point 168 and tip end 166 move through slot or opening 60 in tab member 50 mounted in notch 230 of engagement member 220 and continue to move until the tab member 50 is engaged by the tab capture notch 180 on needle body 162. Release or reversal of the actuation button member 136 causes the shaft and attached placement member 200 to rotate in the opposite direction causing the tab member 50 to disengage from the notch 230 of engagement member 220.

Figure 6A:
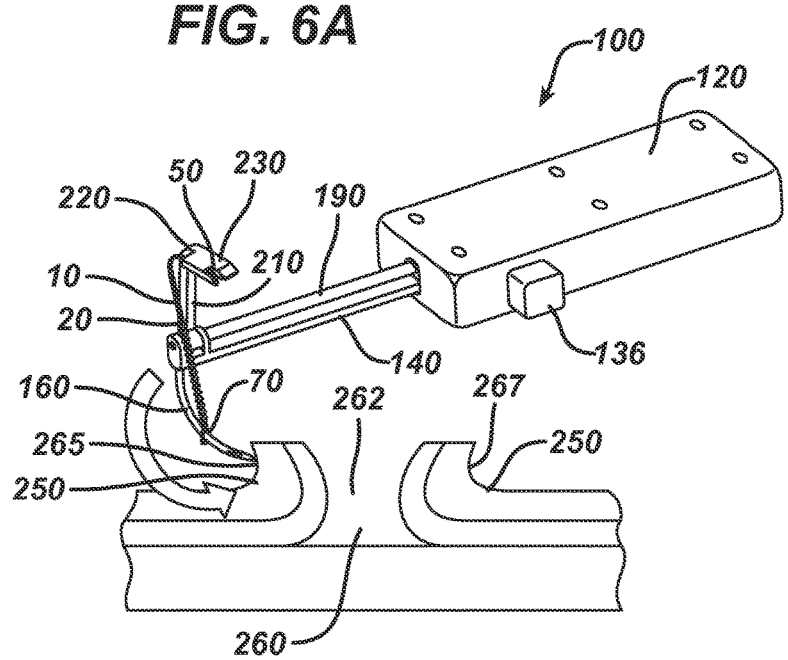
FIGS. 6A-E show a sequence of steps in using the applicator device and tissue wound closure device of FIG. 4 to close a wound in tissue by inserting the tissue wound closure device into and through the tissue about the wound.
Figure 6B:
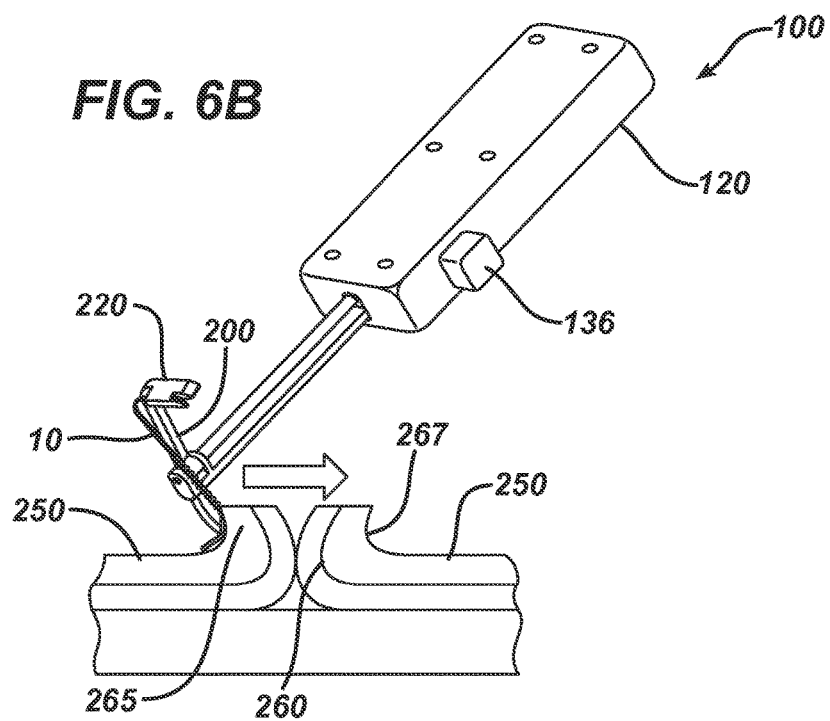
Figure 6C:
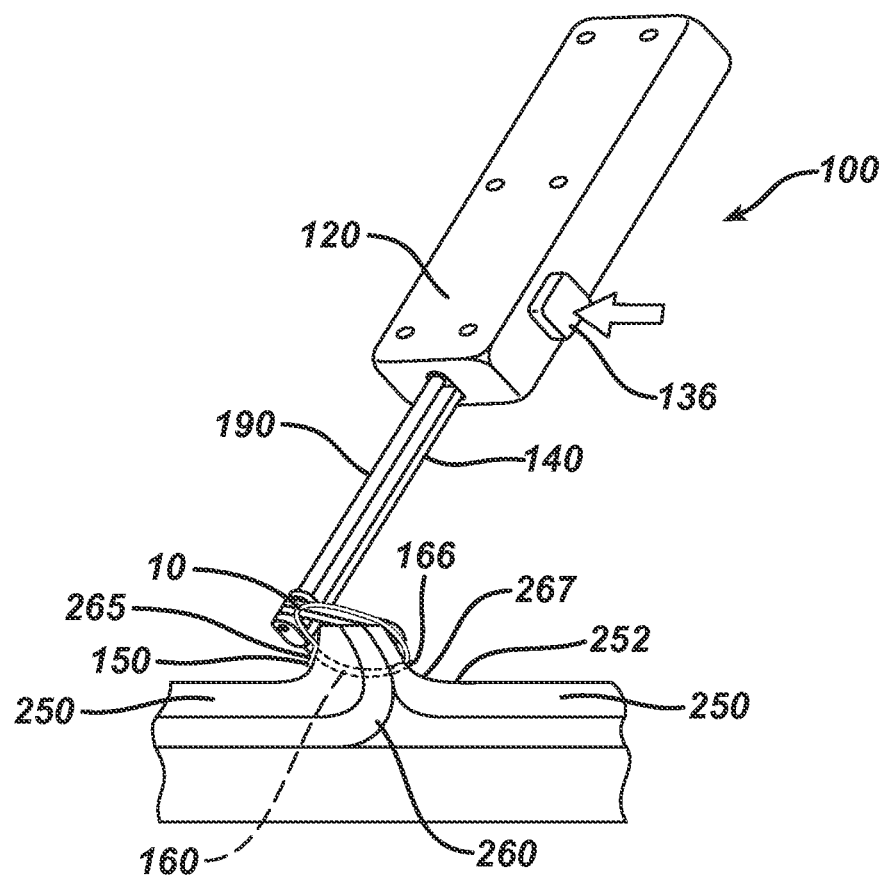
Figure 6D:
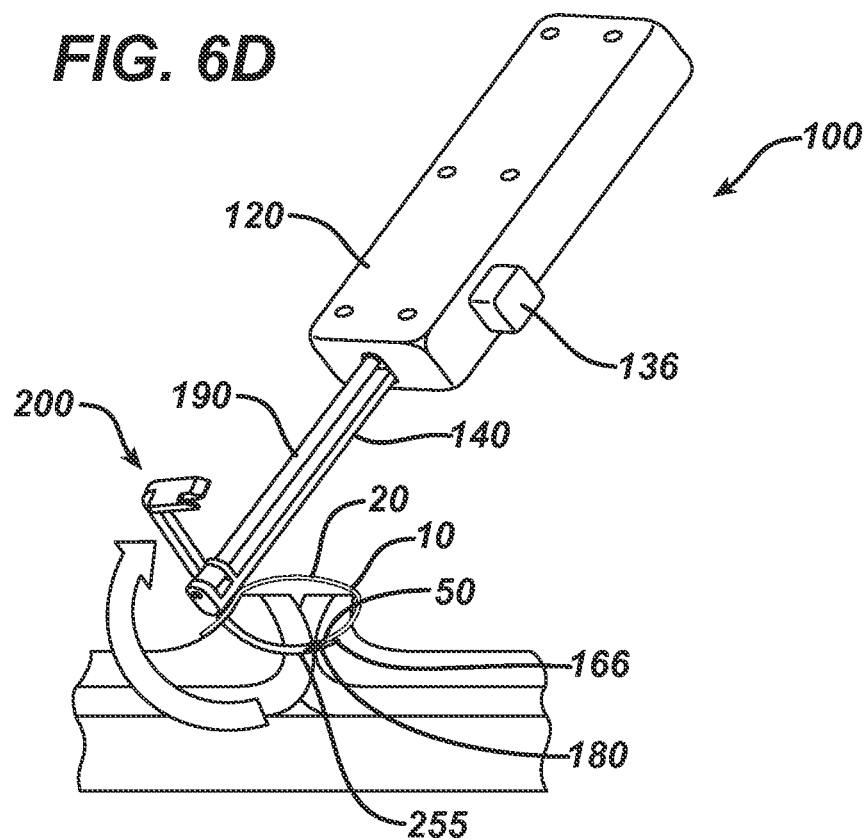
Figure 6E:
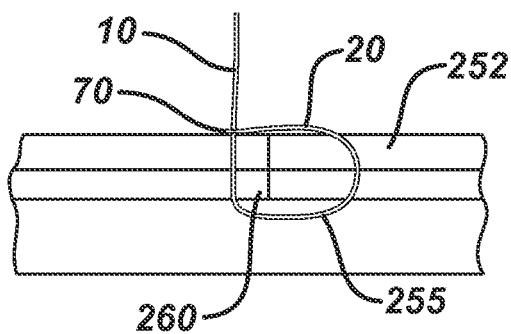
Figure 7:
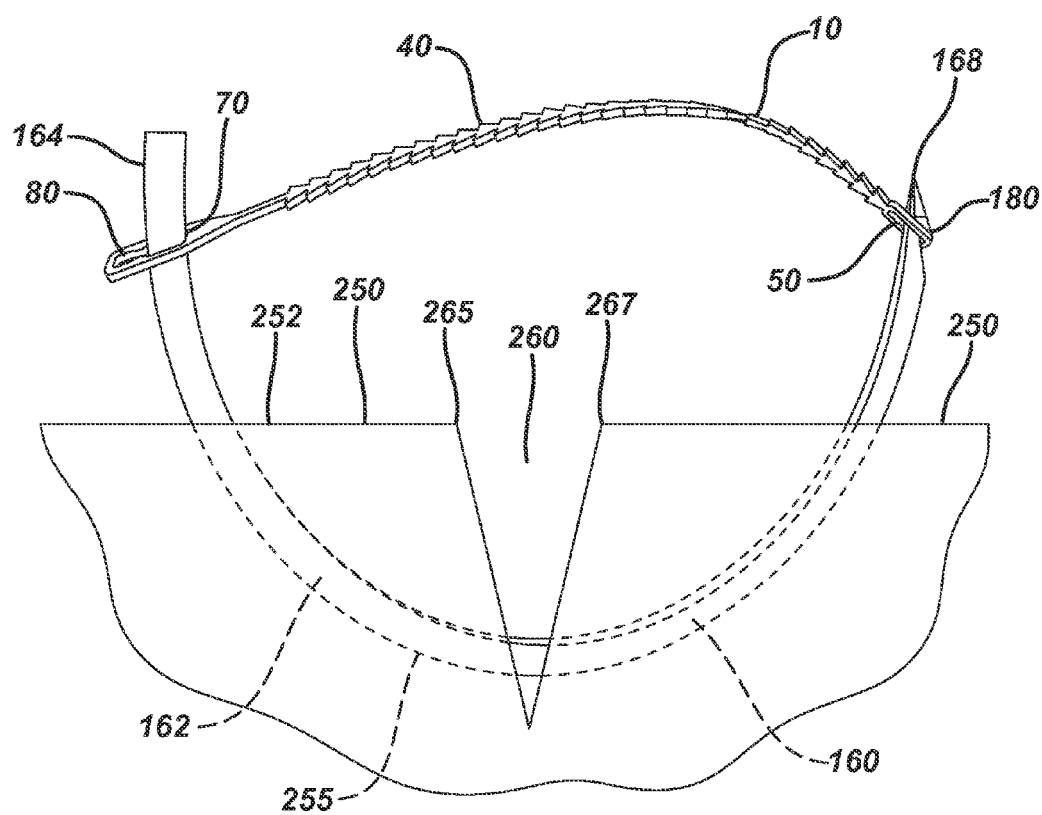
FIG. 7 is a schematic diagram showing the piercing needle of the applicator instrument piercing tissue about a wound. The distal piercing tip of the needle has extended through the tissue. One end of a tissue wound closure device of the present invention is seen to be engaged by a capture notch in the distal end of the needle, while the other end of the tissue wound closure device is seen to be engaged about the proximal end of the needle.
Figure 8:
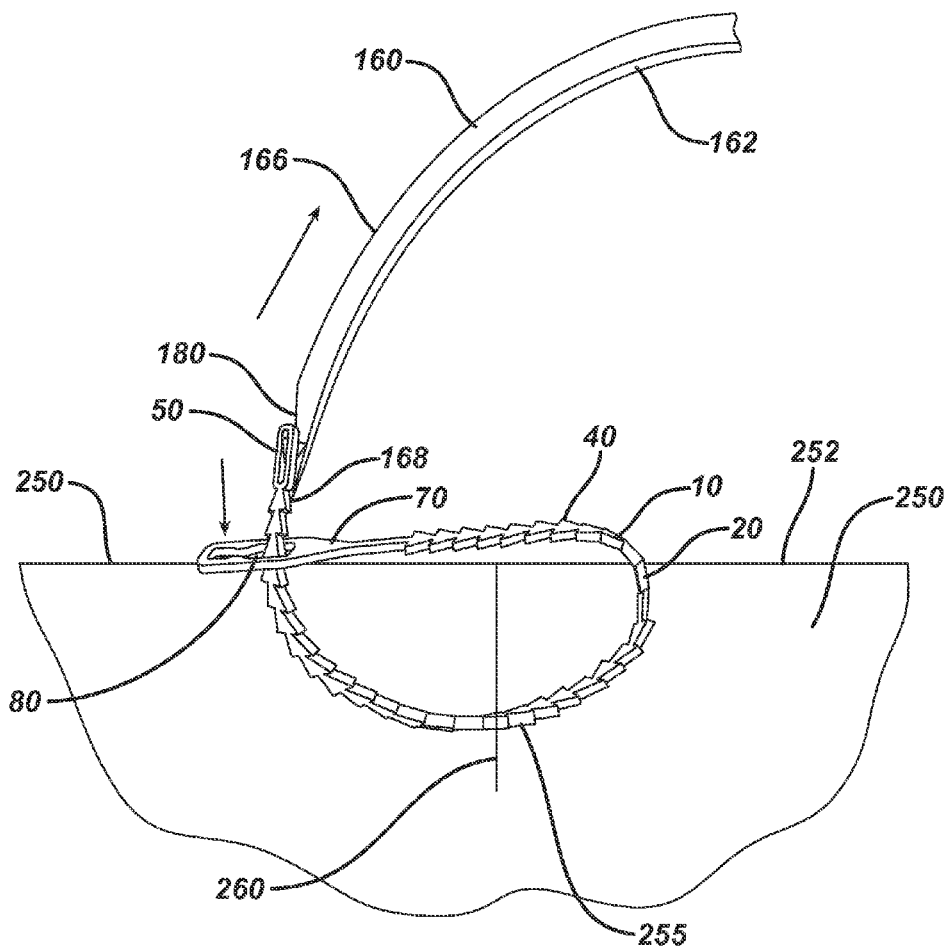
FIG. 8 is a schematic diagram showing the wound in the tissue of FIG. 7 closed by withdrawing the needle out through the tissue and moving a section of the tissue wound closure device through the tissue about the wound and tensioning it. The needle is seen to have passed through the proximal end of the tissue wound closure device along with the distal end of the closure device and a section of the closure device adjacent to the distal end.
Figure 9:
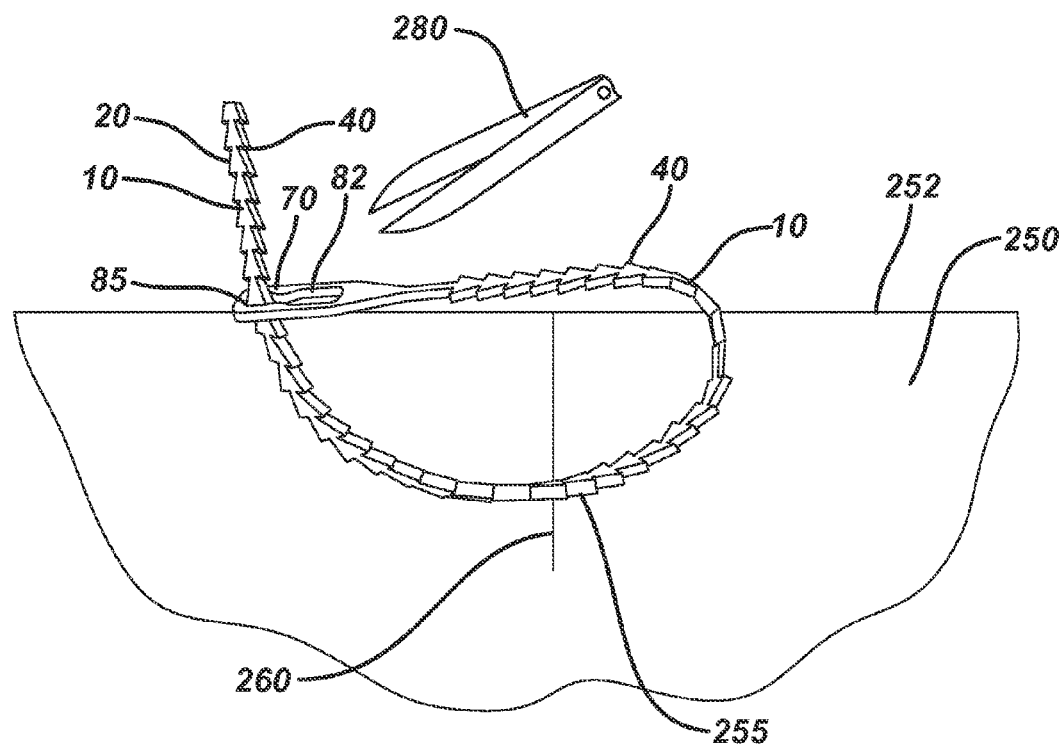
FIG. 9 is a schematic showing the tissue wound closure device of FIG. 8 about the wound in the tissue after the needle has been disengaged with a section of the wound closure device locked in a keyhole opening in the proximal end; a pair of surgical scissors is seen proximate the distal end to cut off the excess length.

The use and function of the tissue wound closure device 10 and applicator 100 of the present invention are illustrated in FIGS. 6A-E, 7, 8 and 9. The device 10 is seen mounted to an applicator instrument 100 in the ready position in FIG. 6A. In this ready position the proximal or second tab member 70 has been slidably mounted onto the needle body 162, while the distal or first tab member 50 has been mounted in notch 230. The instrument 100 and the device 10 mounted to needle member 160 and engagement member 220 are seen to be positioned proximate to wound 260 in tissue 250. The wound 260 is seen to have opening 262 surrounded by opposed first and second wound sides 265 and 267, respectively. The handle member 120 is rotated causing the needle member 160 to rotate and penetrate and grasp tissue 250 on one side 265 of wound 260 as seen in FIG. 6A. Further rotation, as seen in FIG. 6B, causes the wound sides 265 and 267 to be approximated as the needle member moves through the tissue about the wound 260, closing the opening 262, and forming needle tissue pathway 255. The needle member 160 is rotated until the piercing point 168 and distal end 166 exit the tissue surface 252 proximate wound side 267. During these two steps, the proximal tab member 70 is seen to slide rearward along the needle body 162 and remain adjacent to the first wound side 265. Next, as seen in FIG. 6C, the surgeon engages the push button actuation member 130 causing the shaft 190 and attached placement member 200 to be rotated toward the distal end 166 of the needle member 160 which has penetrated above the surface 252 of the tissue 250 adjacent to second wound side 267. After the shaft 190 and the placement member 200 have rotated sufficiently to position the tab member 50 of wound closure device 10 on needle body 162 such that piercing tip 168 and distal end 166 have passed through opening 60, the actuation button is released, while the instrument 100 is rotated in an opposite direction. This causes the distal tab member 50 to engage the tab capture notch 180 as further rotation causes a disengagement from tab holding notch 230 of engagement member 220. Next, as the surgeon rotates the needle member in a reverse manner back through the needle tissue pathway 255 that was initially formed, the tab member 50 and a distal section of the body member 20 move through the tissue until exiting from the initial penetration point next to wound side 265. The piercing point 168 and distal end 166 enter the opening 80 of proximal tab member 70 and the device is tightened by providing additional rotation and commensurately moving an additional length of the body member 20 through opening section 82 of keyhole opening 80 until the desired tension and tissue approximation is obtained. Then the surgeon locks the device 10 in place about the wound 260 by manipulating the section of body member 20 from opening section 82 into locking opening 85. At this point, the surgeon then clips off the excess length of the body member 20 adjacent to the tissue surface 252 with surgical scissor 280 and the tissue approximation is complete. Additional tissue wound closure devices 10 may need to be applied to close the opening 262 in the wound 260, depending upon the nature and severity of the wound 260. It should be noted that in FIGS. 7 and 8, the capture notch 180 is illustrated located alternatively in the outer surface 172 of needle body 162, while in FIGS. 6 A-E the capture notch 180 is illustrated in the interior surface 170 of needle body 162

Figure 10:
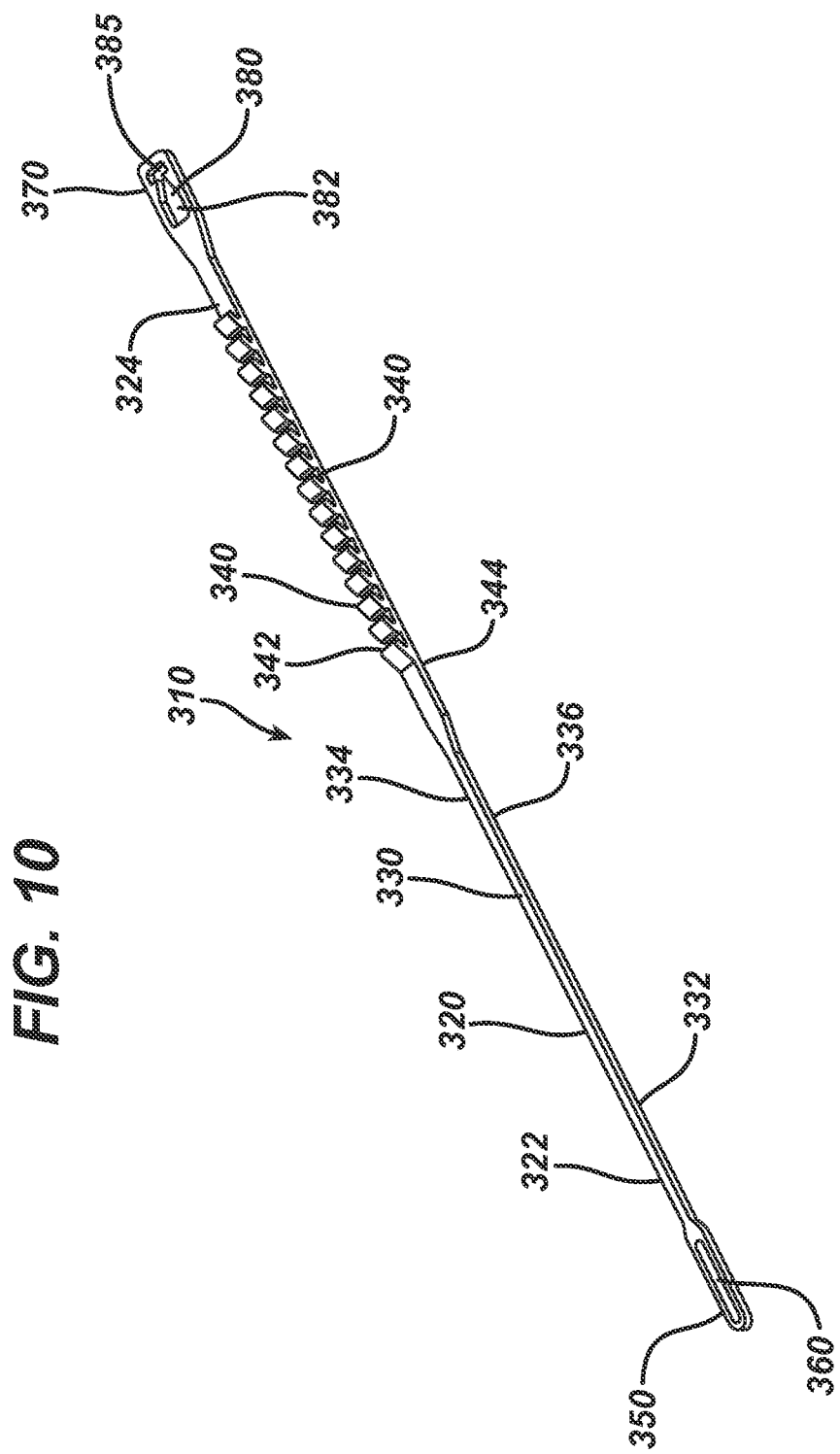
FIG. 10 is a perspective view of an alternate embodiment of a tissue wound closure device of the present invention. The device has barbs extending from atop surface.
Figure 11:
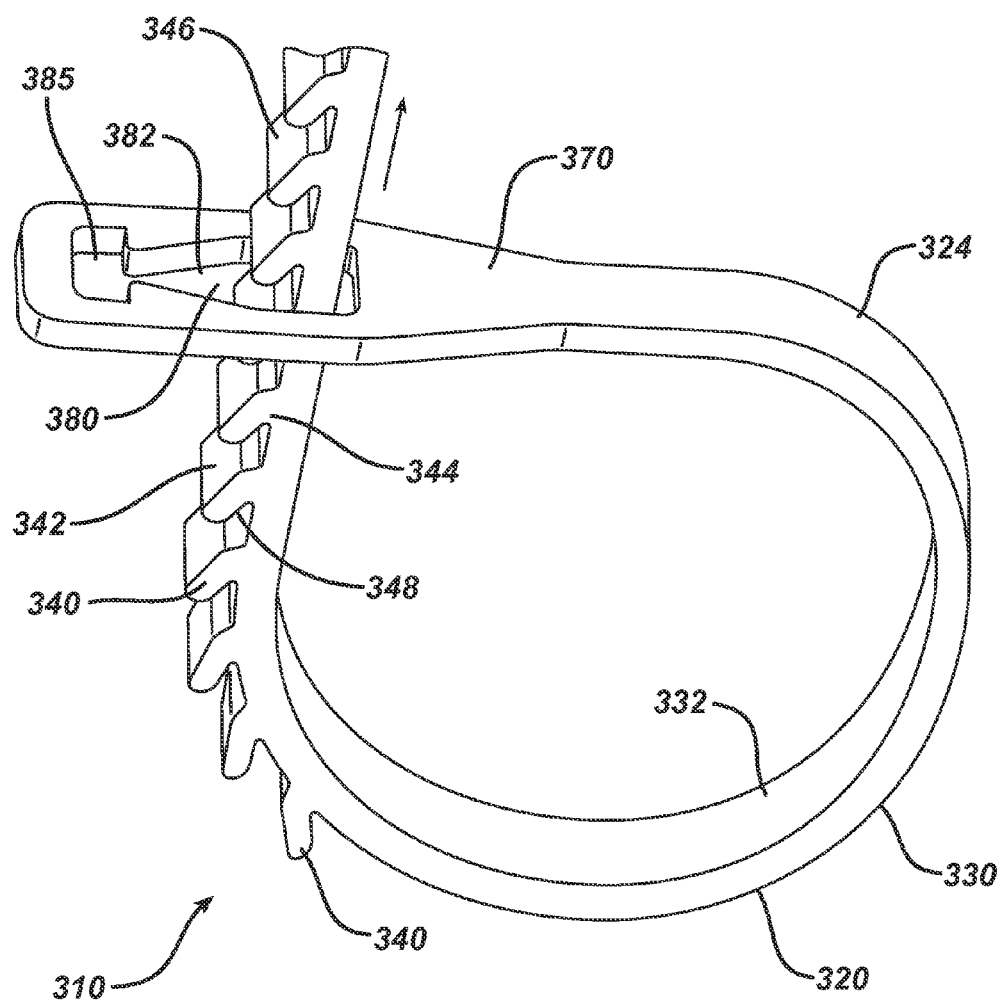
FIG. 11 is a schematic diagram of the wound closure device of FIG. 10 showing a distal section of the device passing through a keyhole opening in the proximal end of the device.
Figure 12:
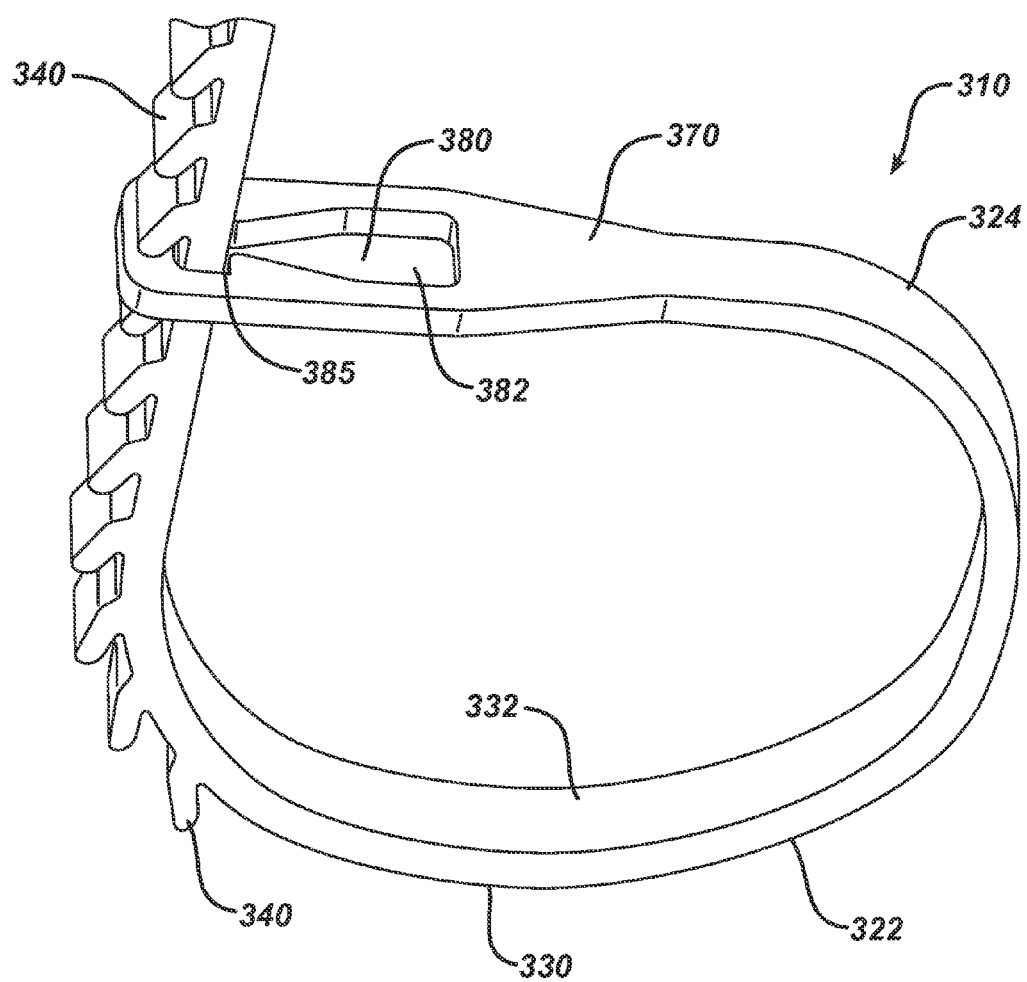
FIG. 12 is a schematic view of the device of FIG. 11 showing a section of the tissue closure device locked in the keyhole opening.

An alternate embodiment of a wound tissue closure device of the present invention is seen in FIGS. 10, 11 and 12. The closure device 310 is seen to have elongated body member 320. Body member 320 is seen to have distal end 322 and proximal end 324. The body member has top surface 330, bottom surface 332 and opposed lateral sides 334 and 336. Extending upwardly from a section of the top surface 330 are a plurality of barb members 340. If desired, the barb members 340 may extend along the entire length of member 320. The barb members 340 have distal ends 342, proximal ends 344 and top and bottom sloping surfaces 346 and 348 connecting the distal ends 342 and proximal ends 344. As shown, the body member 320 is flat. If desired, body member 320 may have a round, curved, or polygonal cross-section, and the barb members 340 may have other equivalent geometric shapes. Extending from the distal end of 322 of the body member 320 is the distal tab member 350. Tab member 350 is seen to have a slot or opening 360 for receiving a section of the body member 320 including barb members 340. Opening 360 is sufficiently sized to allow movement of the body member 320 and barbs 340 through the tab member 350. Proximal tab member 370 is seen to extend from the proximal end 324 of the body member 320. Tab member 370 is seen to have keyhole opening 380 for receiving and locking a section of body member 320. The opening 380 has enlarged opening section 382 for receiving a section of body member 320 and smaller locking opening 385 in communication with section 382 for receiving and locking a section of body member 320. Opening 382 is sufficiently sized to allow movement of the body member 320 and barbs 340 through the tab member 370.

Figure 13:
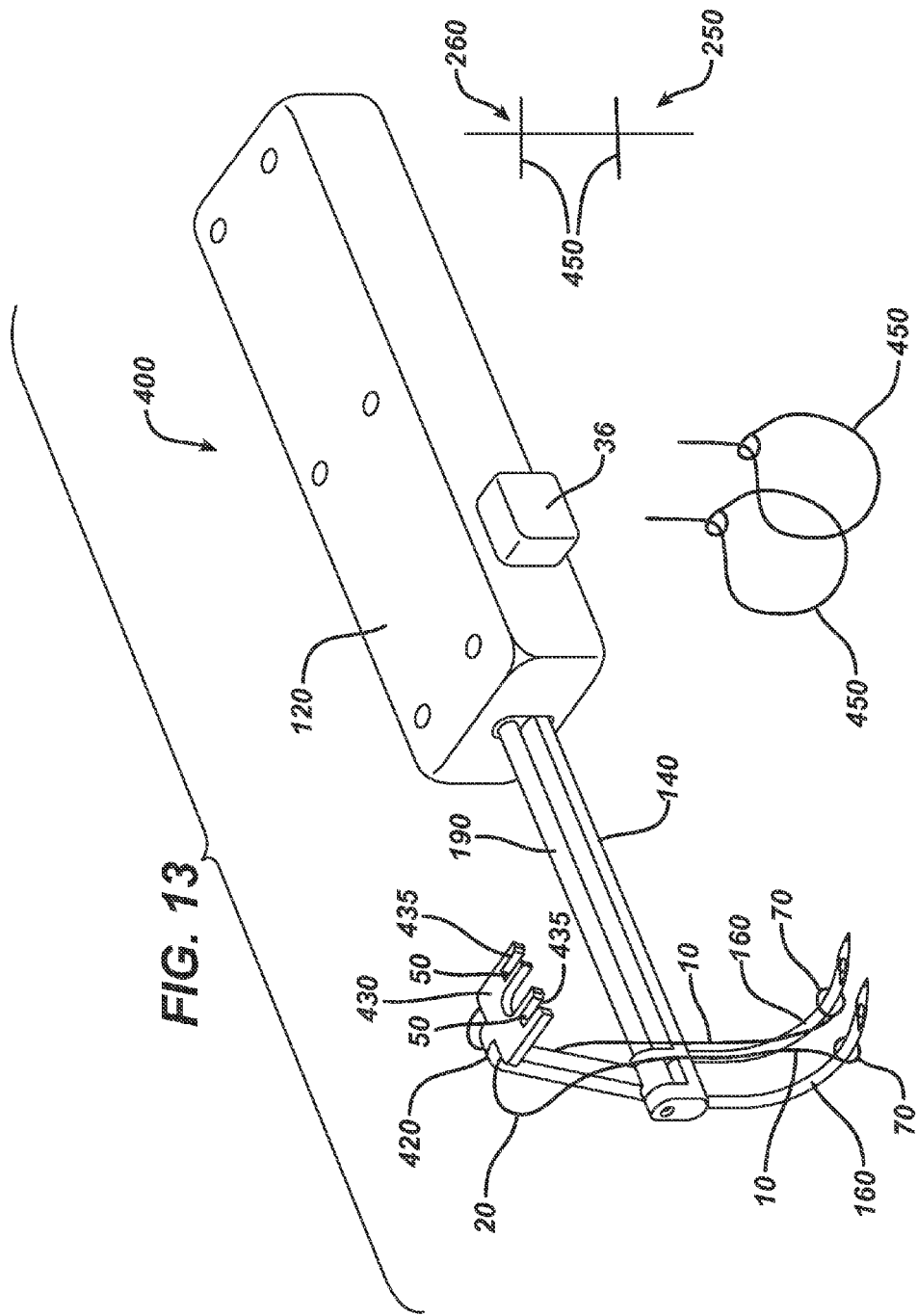
FIG. 13 is a perspective view of an alternate embodiment of an applicator instrument configured to mount two tissue wound closure devices of the present invention. The device will provide two interrupted stitches in tissue as shown schematically.
Figure 14:
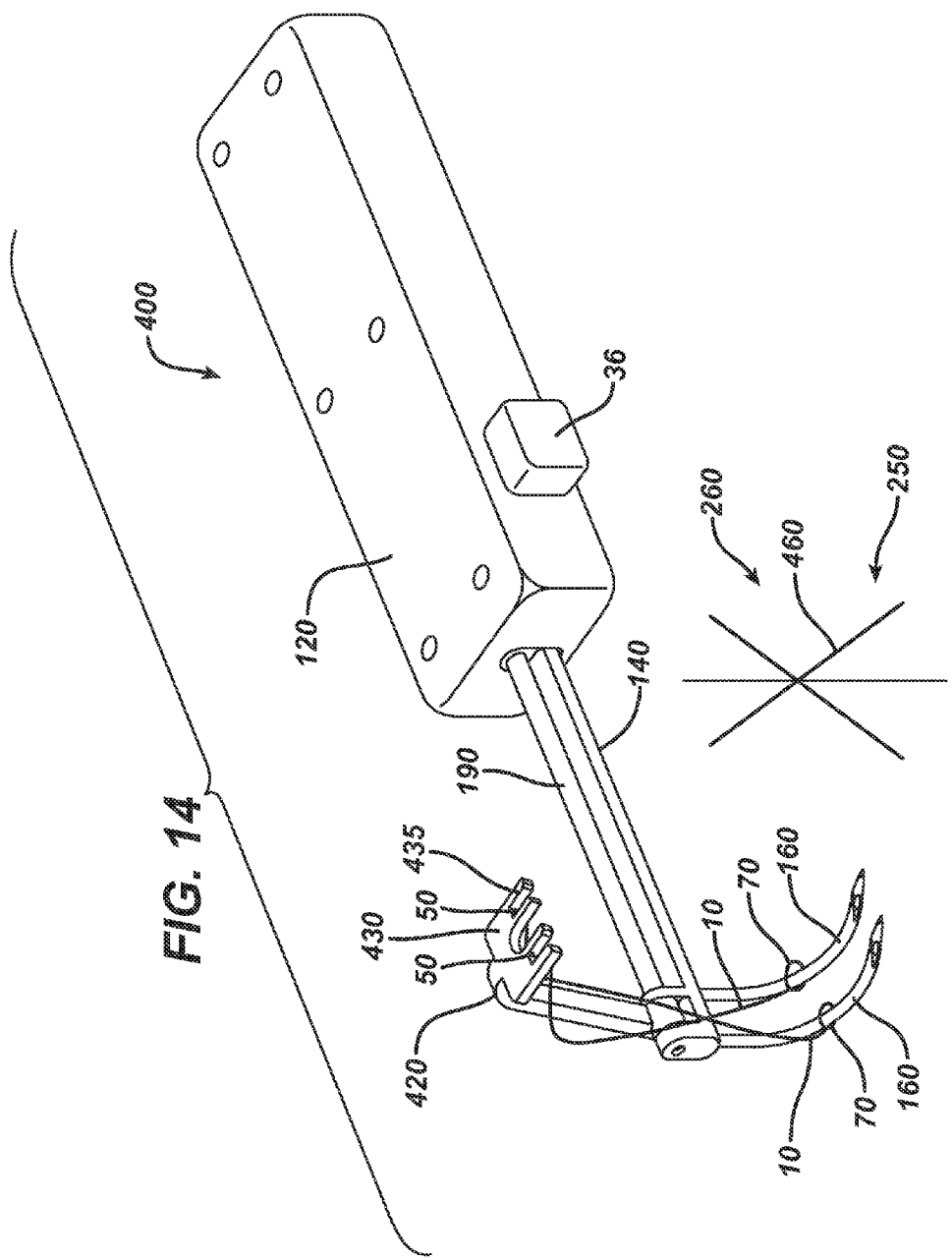
FIG. 14 illustrates the applicator device of FIG. 13 having two wound closure devices of the present invention mounted in a crisscross manner. The device will provide across-stitch in tissue as shown schematically.

An alternate embodiment of an applicator device 400 of the present invention loaded with multiple tissue wound closure devices 10 of the present invention is seen in FIGS. 13 and 14. The instrument 400 is identical to the instrument 100 except that it is configured to hold two devices 10. The instrument 400 is seen to have two needle members 160 mounted next to each other to cap member 150. The placement member 420 is seen to differ from placement member 200 in that the engagement member 430 has two notches 435 for engaging the distal tab members 50 of two tissue wound closure devices 10, although if desired two placement members 200 could be used. The device 400 operates in a similar manner to applicator instrument 100. However, as seen schematically in FIG. 13, one application cycle of the instrument 400 will result in two devices 10 being implanted about a wound 260 in tissue 250 in an interrupted stitch manner to form interrupted stitches 450. As seen schematically in FIG. 14, mounting the tab members 70 to the needles 160 in a crisscross manner will result in cross-stitch 460 in tissue 250 about wound 260. The instrument 400 can be configured to hold more than two devices 10 by increasing the number of needle members 160 and placement members 200.

The novel tissue wound closure devices and applicator instruments of the present invention have many advantages and benefits. These advantages and benefits include providing an adjustable fastener for wound closure, which is self-knotting. In addition, the systems of the present invention provide the ability to approximate tissue using one hand, create either a single or crossed stitch, and create two or more stitches simultaneously.

Although this invention has been shown and described with respect to detailed embodiments thereof, it will be understood by those skilled in the art that various changes in form and detail thereof may be made without departing from the spirit and scope of the claimed invention.

We claim:

1. An apparatus for applying an elongated tissue closure device, comprising:
    an elongated handle member having a proximal end and a distal end;
    a shaft member rotatably mounted to the handle member and extending from the distal end of the handle member, the shaft member having a longitudinal axis;
    an actuation member moveably mounted to the handle member for engaging a linear to rotary motion mechanism in the handle member to cause the shaft member to rotate;
    a beam member extending from the distal end of the handle member, the beam member having a proximal end and a distal end and a longitudinal axis;
    a first curved needle member defining a plane and having a proximal end, a distal end, an inner surface, an outer surface, a capture notch, and a piercing point extending from the distal end, wherein the proximal end of the curved needle member is mounted to the distal end of the beam member such that the plane of the needle member is substantially transverse to the longitudinal axis of the beam member; and,
    a first placement member mounted to the distal end of the shaft member in a manner substantially transverse to the longitudinal axis of the shaft member, the placement member having a post member, the post member having a distal end, and a tab engagement member having an engagement notch for receiving a tab member extending from the distal end of the post member.

2. The apparatus of claim 1, wherein the actuation member comprises a button member.

3. The apparatus of claim 1, additionally comprising a second curved needle member mounted next to the first curved needle member and a second engagement notch next to the first engagement notch.

4. The apparatus of claim 1, wherein the capture notch is in the inner surface of the needle member.

5. The apparatus of claim 1, wherein the capture notch is located in the distal end of the needle member.

6. A wound closure system, comprising:
A. an apparatus for applying an elongated wound closure device, the apparatus comprising:
an elongated handle member having a proximal end and a distal end;
a shaft member rotatably mounted to the handle member and extending from the distal end of the handle member;
an actuation member mounted to the handle member for engaging a linear to rotary motion mechanism in the handle member to cause the shaft member to rotate;
a beam member extending from the distal end of the handle member, the beam member having a proximal end and a distal end and a longitudinal axis; and,
a curved needle member defining a plane and having a proximal end, a distal end, an inner surface, an outer surface, a capture notch, and a piercing point extending from the distal end, wherein the proximal end of the curved needle member is mounted to the distal end of the beam member such that the plane of the needle is substantially transverse to the longitudinal axis of the beam member; and,
a placement member mounted to the distal end of the shaft member shaft in a manner substantially transverse to the longitudinal axis of the shaft member, the placement member having a post member, the post member having a distal end, and a tab engagement member having an engagement notch for receiving a tab member extending form the distal end of the post member; and,
B. a tissue wound closure device, the wound closure device comprising:
an elongated member having a proximal end, a distal end, opposed lateral side surfaces, a top surface, and a bottom surface;
a first tab member extending from the proximal end, the first tab member having a keyhole opening;
a second tab member extending from the distal end, the second tab member having an opening; and,
a plurality of barb members extending from at least one surface of the elongated member,
wherein the keyhole opening in the first tab member is configured to pass the second tab member through and receive a section of the elongated member, and to lock a section of the elongated member in a fixed position within the first tab member.

7. The system of claim 6, wherein said closure device comprises an absorbable polymer.

8. The system of claim 6, wherein said closure device comprises a non-absorbable polymer.

9. The system of claim 6, wherein the keyhole opening has a first opening for receiving the second tab member and a second opening in communication with the first opening for locking a section of the elongated member.

10. The system of claim 6, wherein the barb members extend from at least part of each lateral side surface.

11. The system of claim 6, wherein the barb members extend from the top surface.

12. The system of claim 6, wherein the actuation member comprises a button member.

13. The system of claim 6, additionally comprising a second curved needle member mounted next to the first curved needle member and a second placement member mounted next to the first placement member.

14. The system of claim 6, wherein the capture notch is in the inner surface of the needle member.

15. The system of claim 6, wherein the capture notch is in the distal end of the needle member.

16. A method of approximating the two tissue edges using the system of claim 6, comprising:
mounting the tissue wound closure device to the apparatus by sliding the proximal tab member over the distal end of the needle body and mounting the distal tab member in the engagement notch of the tab engagement member;
rotating the apparatus in a direction to pass a section of the needle member through tissue about a wound forming a tissue pathway, wherein the tissue has a surface, such that the distal piercing tip and at least the distal end and the capture notch of the needle member extend above a surface of the tissue;
engaging the actuation member to cause the placement member to rotate toward the needle tip and needle distal section such that the needle tip and needle distal section move through the opening in the second tab member;
rotating the apparatus and needle in an opposite direction thereby engaging the second tab member in the needle capture notch and disengaging the second tab member from the engagement notch in the tab engagement member;
moving the second tab member and a section of the elongated member through the tissue pathway and through the keyhole opening in the first tab member; and,
locking a section of the elongated member having barb members in the keyhole opening of the first tab member.

17. The method of claim 16, wherein the keyhole opening comprises a first opening for receiving the second tab member and a second opening in communication with the first opening for receiving and locking a section of the elongated member, and wherein the section of the elongated member having at least one barb is locked in the second opening.

18. The method of claim 16, wherein the applicator additionally comprises a second curved needle member mounted next to the first curved needle member and a second engagement notch located next to the engagement notch, and a wound closure device is mounted to each curved needle member.

* * * * *